(12) United States Patent
Geffard et al.

(10) Patent No.: US 10,151,689 B2
(45) Date of Patent: Dec. 11, 2018

(54) METHOD FOR IDENTIFYING AND CHARACTERIZING POLYLYSINE COMPOUNDS

(71) Applicant: GEMAC, Saint Jean d'illac (FR)

(72) Inventors: Michel Geffard, Talence (FR); Laetitia Vidal, Villenave d'ornon (FR)

(73) Assignee: GEMAC, Saint Jean d'Illac (FR)

( * ) Notice: Subject to any disclaimer, the term of this patent is extended or adjusted under 35 U.S.C. 154(b) by 0 days.

(21) Appl. No.: 15/503,604

(22) PCT Filed: Aug. 6, 2015

(86) PCT No.: PCT/FR2015/052165
§ 371 (c)(1),
(2) Date: Feb. 13, 2017

(87) PCT Pub. No.: WO2016/024062
PCT Pub. Date: Feb. 18, 2016

(65) Prior Publication Data
US 2017/0241903 A1  Aug. 24, 2017

(30) Foreign Application Priority Data
Aug. 11, 2014 (FR) ..................... 14 57736

(51) Int. Cl.
| | |
|---|---|
| *G01N 21/35* | (2014.01) |
| *G01N 21/33* | (2006.01) |
| *G01N 30/30* | (2006.01) |
| *G01N 30/88* | (2006.01) |
| *G01N 21/3563* | (2014.01) |
| *G01N 21/3577* | (2014.01) |

(52) U.S. Cl.
CPC ............ *G01N 21/35* (2013.01); *G01N 21/33* (2013.01); *G01N 21/3563* (2013.01); *G01N 21/3577* (2013.01); *G01N 30/30* (2013.01); *G01N 30/88* (2013.01); *G01N 2021/3595* (2013.01); *G01N 2030/8831* (2013.01)

(58) Field of Classification Search
CPC ... G01N 2021/3595; G01N 2030/8831; G01N 21/33; G01N 21/35; G01N 30/30; G01N 30/88
See application file for complete search history.

(56) References Cited

FOREIGN PATENT DOCUMENTS

WO    WO 2007127977 A2 * 11/2007 ......... G01N 33/6806

OTHER PUBLICATIONS

Vidal et al., "Lauryl-poly-L-lysine: A New Antimicrobial Agent?", Feb. 23, 2014, Journal of Amino Acids, vol. 2014, pp. 1-10.*

* cited by examiner

*Primary Examiner* — Mark R Gaworecki
(74) *Attorney, Agent, or Firm* — Young & Thompson

(57) ABSTRACT

Disclosed is a method for identifying and characterizing compounds conjugating at least one polylysine and at least one other molecule chosen from the acids, fatty acids, vitamins, amino acids, amino acid derivatives having a neurotransmitter activity and the active substances having a therapeutic effect, the method including at least: a step of identification, by infrared spectroscopy, and at least one characterization step chosen from: ultraviolet-visible absorption spectroscopy, gas phase chromatography, high-performance liquid phase chromatography.

20 Claims, 4 Drawing Sheets

METHOD FOR IDENTIFYING AND CHARACTERIZING POLYLYSINE COMPOUNDS

FIELD OF THE INVENTION

This invention relates to the identification and the characterization of compounds that conjugate at least one polylysine and at least one other molecule.

BACKGROUND OF THE INVENTION

The polypeptide compounds consist of an assembly of homologous or heterologous amino acid units onto which molecules are grafted whose biological and/or pharmacological activity is preserved.

It may involve, for example, polylysine compounds. These compounds have been described in particular in the patent FR9413861.

The polypeptide compounds such as polylysine can be used for numerous biological, food-processing, medical, pharmaceutical, cosmetic and environmental applications.

So that these compounds are distributed as raw materials for these applications, in particular as raw materials for pharmaceutical usage (RMPU), it is necessary to be able to issue reliable analytical reports making possible their identification and their characterization. Today, however, there is no specific method that makes it possible to identify and to characterize in a reliable, pertinent, and rigorous way the polypeptide compounds that are substituted in general and polylysine compounds in particular. Analytical proposals have been carried out for these compounds, but none are satisfactory.

It is possible to cite, for example, the study carried out in 2002 by the Waters Company (St. Quentin en Yvelines (78)), which describes in particular the identification of components grafted onto polylysine, by coupling liquid chromatography and positive and negative electrospray mass spectrometry, but this method does not make it possible to separate the analytes correctly. Likewise, a study carried out in 2003 by NMR (nuclear magnetic resonance) DOSY ("Diffusion Ordered Spectroscopy"), the NMRtec laboratory of the Montpelier Pharmaceutical Department (34), according to the NMR DOSY analytical report of GEMSEP01b, reference 20030739, describes a method that makes it possible to detect the presence of polylysine compounds that are expected in the mixture, to identify the skeleton of the polylysine, but this method does not make it possible to identify in a reliable way the different molecules that are grafted with low concentrations of the preparation.

The use of the electrospray liquid chromatography technique coupled to a mass spectrometer (HPLC/ESI/QTOF-MS) was reevaluated and also described in the report of the Université René DESCARTES, Paris V, Pharmaceutical Department (75) in 2003-2004. There again, this method does not make it possible to quantify the grafted molecules of the polylysine compounds.

The verification of the grafting of haptenes onto polylysine was also carried out by a MALDI-TOF and MALDI/MS mass spectrometer in the laboratory of the Institute of Molecular Sciences of the Université de Bordeaux (33) in 2005 and 2008.

This technique confirms the presence of small grafted molecules but did not allow them to be identified and characterized.

The method by steric exclusion chromatography (SEC) has also been tested according to the results of the Université de Bordeaux, but it did not provide any significant results relative to polylysine and its compounds.

It is also possible to cite the implementation of immunoenzymatic metering by Elisa test of polylysine compounds grafted with amino acids according to a report from the Gemac Company for the clinical test of 2003, No. 2002SEP01. Although this method made it possible to calculate the curve of the metering of the compound that is grafted onto polylysine, it did not make it possible to identify and meter the grafted molecules/polylysine ratio correctly. In addition, this method does not demonstrate possible molecular artifacts.

Other techniques have been tested, but none of these methods is reliable and can be applied to all of the polypeptide compounds grafted with various molecules.

SUMMARY OF THE INVENTION

The objective of the invention is consequently to compensate for the lack of analytical methods and to propose a method that makes it possible to identify and to characterize polypeptide compounds, in particular polylysines, in a reliable, simple, reproducible, and universal way, for the purpose of their certification and their applications.

For this purpose, the object of the invention is a method for identification and characterization of compounds that conjugate at least one polylysine and at least one other molecule that is selected from among the acids, fatty acids, vitamins, amino acids, metabolic derivatives of amino acids that have a neutrotransmitter effect, and the active substances that have a therapeutic effect, comprising at least:
one step for identification by infrared (IR) spectroscopy, and
at least one step for characterization selected from among:
absorption spectroscopy in the visible ultraviolet,
gas phase chromatography,
high-performance liquid phase chromatography.

Advantageously, this method comprises the implementation of known and simple analytical methods, which, combined with one another, make possible the identification, the quantification, and the reproducibility in a universal and reliable way of polylysine conjugates, as well as the characterization of organic impurities resulting from their manufacture and purification. The implementation of this method makes it possible to compile analytical reports of polylysine conjugates and consequently allows their use for regulated usage—in particular in the pharmaceutical field—of food supplements, which was not possible up until then.

BRIEF DESCRIPTION OF THE DRAWINGS

Other characteristics and advantages will emerge from the following detailed description of the invention, relative to the accompanying figures in which.

DETAILED DESCRIPTION OF THE INVENTION

Figure 1:
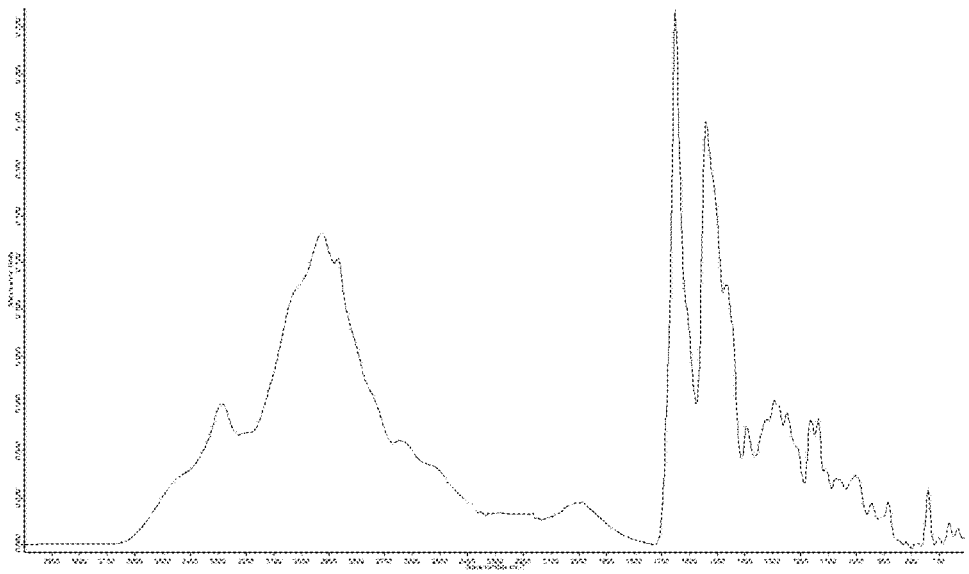
FIG. 1 shows an IR spectrum of polylysine.

The object of the invention is therefore a method for identification and characterization of compounds that have at least one polylysine and at least one other molecule that is selected from among acids, fatty acids, vitamins, amino acids, metabolic derivatives of amino acids that have a neurotransmitter activity, and the active substances that have a therapeutic effect and that comprise at least:
  one step for identification by IR spectroscopy, and
  at least one step for characterization selected from among:
    absorption spectroscopy in the visible ultraviolet,
    gas phase chromatography,
    high-performance liquid phase chromatography.

In terms of the invention, identification is defined as the determination of the identity of the analyzed compounds. It consists in verifying the presence of polylysine and in identifying the nature of the grafted molecules.

In terms of the invention, characterization is defined as the determination of additional characteristics relative to the analyzed compounds, such as the content of molecules grafted onto the polylysine, the quantity of impurities of synthesis, the monitoring of raw materials, the secondary structure, etc. This characterization is an analytical process that implements physico-chemical techniques of instrumental analyses that are qualified according to the ICH (International Conference on Harmonization) recommendations that are the most suitable and that make possible a reliable, robust, and specific analysis of the analyzed compounds.

The molecule or molecules grafted onto the polylysine are preferably molecules that have a molecular weight of less than 900 g/mol. The metabolic derivatives of amino acids that have a neurotransmitter activity are preferably metabolic derivatives of amino acids that have a neurotransmitter effect that originates from the metabolic paths of tryptophan hydroxylase, tyrosine hydroxylase, glutamate decarboxylase, and/or histidine decarboxylase.

The active substances that have a therapeutic effect can be molecules or sets of molecules that have a therapeutic effect in man or animal.

The polylysine is a linear or branched macromolecule of lysine units, preferably L-lysine (poly-L-lysine), whose number (n) of sub-units is preferably at least 30 lysines: n≥30 lysines.

The method according to the invention comprises a step for identification of the compound by IR (infrared) spectroscopy.

The IR spectroscopy is a technique that is known both in industry and research as quality control or a research measure. Its use is simple and quick, reproducible and reliable. This technique does not destroy the sample, with little or no preparation of the sample. The samples can be analyzed in the form of powder, liquid, film or gas, according to the accessories of the sample compartment. The equipment and the software are easily used in routine analysis.

Its use in the method according to the invention makes possible the identification of all of the polylysine compounds, the determination of the composition of the sample, and the quantification of the components. The objective of the characterization is to identify the spectral fingerprint of the polylysine compound. The step for identification by IR spectroscopy consists in comparing the spectrum obtained for the polylysine/molecule conjugate in the polylysine spectrum and in the spectrum of the molecule by itself. Actually, the grafting of the molecule onto the polylysine is verified by comparison with the IR fingerprint of the polylysine, of the small molecule by itself, and a monitoring of the mixture type of the free molecule with the free polylysine. The peaks specific to the small molecule are thus restored. All of the polylysine compounds can be identified and recognized by their IR fingerprints. According to the IR spectrum, the general and majority of the spectral fingerprint of a polylysine compound is that of the polylysine.

In a preferred way, the IR spectroscopy is a Fourier Transform Infrared spectroscopy. The polylysine compounds are thus analyzed by Fourier Transform Infrared (FT-IR) equipment and in particular using the ATR ("Attenuated Total Reflectance") accessory.

This step for identification by IR spectroscopy is preferably implemented with at least one of the following characteristics:
  spectral range of between 400 and 4000 cm$^{-1}$,
  a spectral intensity in terms of transmission or absorbency,
  a resolution of between 1 and 8 cm$^{-1}$,
  a number of scans carried out by the equipment of between 10 and 20, for each analyzed sample.

The analysis of the polylysine compounds and raw materials is done in the form of powder or liquid in a spectral range preferably going from 400 to 4000 cm$^{-1}$. A background is produced before each analysis; the parameters of the spectra are by wave number (cm$^{-1}$) for the abscissa and by absorbency or transmittance for the ordinate. Preferably, at least 2 analyses are produced on each sample. A spectrum is recorded in a library that is created for each family of polylysine compounds for the purpose of a subsequent search.

The method according to the invention, in addition to the step for identification by IR spectroscopy, comprises at least one step for characterization selected from among:
  the absorption spectroscopy in the Ultraviolet (UV) and the visible ranges,
  gas phase chromatography, and
  high-performance liquid phase chromatography (HPLC).

The method according to the invention can also comprise a step for detecting residual solvents and/or at least one microbiological monitoring by identification of specified microorganisms on an agar medium, ensuring the quality of the polylysine compounds.

The absorption spectroscopy step in the ultraviolet and the visible ranges is a method based on the property that certain molecules have of absorbing light radiation of a determined wavelength. The absorbency of the small molecule grafted onto the polylysine in the field of the ultra-violet will make it possible to calculate its concentration, thanks to the Beer-Lambert law, $A=\varepsilon Cl$, with A being the absorbency or optical density (OD), C being the concentration in mol/L, $\varepsilon$ being the molar absorption coefficient in mol$^{-1}$·L·cm$^{-1}$, and l being the optical path cm$^{-1}$. The absorption spectroscopy in the ultraviolet and the visible ranges is particularly suitable for the polylysine compounds with a grafting of small molecules that have a cycle, such as phenylalanine, L-Dopa, retinoic acid, alpha-tocopherol, 5-methoxytryptamine, etc.

The molar absorption coefficient is calculated using a range of concentrations of the small molecule by itself. This coefficient is applied to the polylysine compound, knowing that a shift of the small molecule is sometimes identified when it is grafted onto a conveyor. Preferably, the spectroscopy step in the UV and the visible ranges is carried out with at least one of the following characteristics:
 implementation on a double-beam spectrometer,
 a spectral range of between 200 and 700 nm,
 a spectral intensity in terms of absorbency,
 a bandwidth of between 1 and 4 nm,
 an acquisition speed of between 120 and 480 nm/minute,
 a volume used of between 700 µl and 2 ml.

Chromatography is defined as a method that makes it possible to separate the components of a mixture that is to be analyzed using their differential migration along a separator device. This separator device is in any case a chromatographic column; it may have the shape of a more or less long cylinder. Reversible physico-chemical equilibrium processes are at the origin of chromatographic separations and more particularly the covalent and primarily non-covalent chemical bonds. Actually, chromatography uses all of the possible forms of reversible interactions between the molecules of the stationary phase and those of solute.

Gas phase chromatography requires evaporating the sample to be analyzed before its injection into the column. To do this, the sample is to be heated. This assumes that the molecules of interest are not degraded at the temperature that is used for evaporating the sample. In general, the gas that is used is the most neutral possible. Most often, helium or nitrogen is used. Hydrogen also has very advantageous characteristics, but since it is a dangerous gas (risk of explosion), it is much less widely used.

Acid hydrolysis is necessary before implementing the gas phase chromatography so as to cut the covalent bond between the fatty acid, the acid, for example, and the polypeptide. For this purpose, it is possible to use methanesulfonic acid. A decanting is then preferably carried out by washing with an organic solvent, before carrying out analysis by chromatography.

The gas phase chromatography step is preferably carried out with at least one of the following characteristics:
 implementation on a semi-capillary column of molten or capillary silica,
 use of a hydrogen or helium vector gas with a flow rate of between 1 and 4 ml/minute,
 a pressure of between 2 and 3 bars,
 a split mode, a temperature of the injector and the detector of between 80 and 300° C., a temperature of the furnace of between 200 and 250° C.,
 a rise in temperature of between 10 and 20° C./minute,
 an injected volume of 2 to 20 µl,
 a flame ionization detector or mass spectrometer.

The high-performance liquid phase chromatography is preferably used in reverse phase. The characteristics are to have an apolar stationary phase and a polar or slightly polar mobile phase, with the most apolar compounds being eluted last. The separation columns that are used are often fine particles of silica gel having —OH groups on the apolar chains (alkyls of C4, C6, C8, C18, phenyl, cyano, etc.). In addition to the fact that this makes the substrate apolar, this also makes it possible to stabilize it over time. Based on grafted chains, more or less hydrophobic columns that will be selected depending on the nature of the molecules to be separated are obtained.

The liquid chromatography (HPLC) analyses should preferably be preceded by an acid hydrolysis and/or derivatization, in particular with a methanesulfonic acid. The high-performance liquid phase chromatography step is preferably carried out with at least one of the following characteristics:
 implementation on a column in normal or reverse phase with a diameter of between 4 and 20 mm, with a length of between 15 and 30 cm,
 use of a polar or slightly polar mobile phase,
 an isocratic mode or gradient,
 an injected volume of 10 to 100 µl,
 a fluorescence detector or visible UV detector.

According to a first embodiment, the compounds that are to be identified and characterized are compounds that have at least one polypeptide and at least one acid and/or at least one fatty acid, and the method according to the invention comprises at least one IR spectroscopy step, and a gas phase chromatography step preceded by an acid hydrolysis.

According to a second embodiment, the compounds that are to be identified and characterized are compounds that have at least one polypeptide and at least one vitamin, and the method according to the invention comprises at least one IR spectroscopy step, and:
 a step of absorption spectroscopy in the UV and the visible ranges, and/or
 a step of gas phase chromatography or a step of high-performance liquid phase chromatography.

According to a third embodiment, the compounds that are to be identified and characterized are compounds that conjugate at least one polylysine and at least one acid, and the method according to the invention comprises at least one IR spectroscopy step and one high-performance liquid phase chromatography step.

According to a fourth embodiment, the compounds that are to be identified and characterized are compounds that conjugate at least one polylysine and at least one derivative of amino acids with a neurotransmitter activity, and the method according to the invention comprises at least one IR spectroscopy step, and:
 a step of absorption spectroscopy in the UV and the visible ranges, and/or
 a step of high-performance liquid phase chromatography (HPLC).

The different preferred embodiments of the method according to the invention are summarized in the table below:

|  | Fatty Acids Acids | Vitamins | Amino Acids | Neurotransmitters |
|---|---|---|---|---|
| Identification |  | IR |  |  |
| Quantification | GPC | Visible UV and/or GPC or HPLC | HPLC | Visible UV and/or HPLC |

IR = Infrared
Visible UV = Absorption spectroscopy in the UV and the visible ranges
GPC = Gas Phase Chromatography
HPLC = High-Performance Liquid phase Chromatography These different variants can also comprise in addition to the steps already described, a step of search for residual solvents and/or at least one microbiological monitoring by identification of microorganisms in the polylysine compounds.

The active substances should be monitored based on residual solvents according to the requirements relative to the ICH (International Conference on Harmonization) recommendations, corresponding to the limits in solvent content in the form of traces that may remain after synthesis and purification.

According to the classification of residual solvents based on the evaluation of the risk:
- class 1: solvents to avoid,
- class 2: solvents with limited use for pharmaceutical usage,
- class 3: solvents with use limited by Good Manufacturing Practices.

For example, dimethyl sulfoxide is of class 3, methanol is of class 2, ethyl chloroformate is of class 3, triethylamine is of class 2, and glutaraldehyde is of class 2.

Advantageously, the method according to the invention makes possible the characterization of molecules grafted onto polylysines and their analytical validation of these compounds for the purpose of industrial applications in particular in biological, food-processing, cosmetic, medical, pharmaceutical, and environmental fields.

The invention is now illustrated by non-limiting examples of the method according to the invention that make it possible to identify and to characterize specifically compounds that conjugate at least one polylysine (PL) and at least one other molecule. Several compounds have been analyzed:

Conjugate of PL+lauric acid: lauric acid (lauryl) is activated by ethyl chloroformate (ECF) that reacts as a coupling agent by activation of the carboxylic acid of fatty acid. The activation is facilitated by the addition of triethylamine. The intermediate product (lauryl-ECF) reacts to the ε-amino group of the lysyl residue by forming an amide bond. Then, the lauryl-PL compound is purified, ideally by tangential ultra-filtering, and then lyophilized if necessary. The lauric acid is then grafted by covalent bond onto the PL.

Conjugate of PL+uric acid: uric acid is activated by its amine group using the carboxyl group of glutaric anhydride (GA). Then, this uric acid-GA intermediate product is activated by ethyl chloroformate (ECF) that reacts as a coupling agent by activation of the carboxylic acid of the acid. The activation is facilitated by the addition of triethylamine. The second intermediate product (uric acid-GA-ECF) reacts to the ε-amino group of the lysyl residue by forming an amide bond. Then, the uric acid-GA-PL compound is purified, ideally by tangential ultra-filtering, and then lyophilized if necessary. The uric acid is then grafted by covalent bond onto the PL.

Conjugate of PL+ascorbic acid: ascorbic acid is activated by the carbodiimide (EDC) that reacts as a coupling agent by activation of the acid of the compound. This activation is facilitated by the addition of N-hydroxysuccinimide (NHS). The intermediate product reacts to the ε-amino group of the lysyl residue by forming an amide bond. Then, the ascorbate-PL compound is purified, ideally by tangential ultra-filtering, and then lyophilized if necessary. The ascorbic acid is then grafted by covalent bond onto the PL.

Conjugate of PL+5-hydroxytryptamine (5HT): the 5HT is activated by the glutaraldehyde (G) that reacts as a coupling agent by activation of the amine of the amino acid. The intermediate product (5HT-G) reacts to the ε-amino group of the lysyl residue by forming an amide bond. Then, the 5HT-G-PL compound is purified, ideally by tangential ultra-filtering, and then lyophilized if necessary. The 5HT is then grafted by covalent bond onto the PL.

Identification of Polylysine Compounds by Infrared

All of the polylysine compounds are analyzed by means of the Fourier Transform Infrared equipment (FT-IR Bruker) using the ATR ("Attenuated Total Reflectance") accessory. The objective of the characterization is to identify the spectral fingerprint of the PL compound. The grafting of the small molecules onto the PL is verified by comparison with the IR fingerprint of the PL, small molecules by themselves, and a control. The specific peaks due to the small molecules are thus identified. All of the PL compounds can be identified and recognized by their IR fingerprints. According to the IR spectrum, the general and majority of the IR fingerprint of a PL compound is that of the PL.

The analysis of the PL compounds and grafted molecules is done in the form of powder or liquid in a spectral range going from 400 to 4000 $cm^{-1}$. A background is produced before each analysis; the parameters of the spectra are by wave number ($cm^{-1}$) for the abscissa and by absorbency for the ordinate. The resolution is 4 $cm^{-1}$. 16 scans are carried out by the equipment for each analyzed sample. Two analyses on each sample are carried out. A spectrum is recorded in a library that is created for each family of PL compounds. The table below describes the IR standards that make it possible to accept or to refuse a batch of polylysine compounds:

| IR Standards Range of Conformity |
| --- |
| Low value assumed in terms of absorbency: 0.05 Abs to 3300 $cm^{-1}$ 0.180 Abs to 1650 $cm^{-1}$ with baseline correction |
| High value assumed in terms of absorbency: 0.150 Abs to 3300 $cm^{-1}$ 0.450 Abs to 1650 $cm^{-1}$ with baseline correction |
| Verification of grafting: Shift from 2 to 10 $cm^{-1}$ on the amide peaks at 1650 and 1540 $cm^{-1}$ |
| Zone of the specific peaks of the small molecules: Zone of 3000 to 3200 $cm^{-1}$ Zone of 1500 to 600 $cm^{-1}$ |

The spectrum of FIG. 1 is that of the polylysine by itself, shown by the formula:

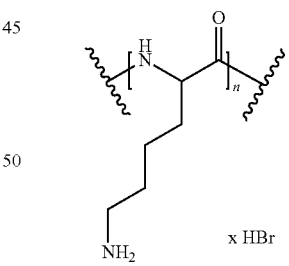

In FIG. 1, the zone of 2600 to 3600 $cm^{-1}$ corresponds to the groups CH and $CH_2$ that are present in the PL. For each functional group, a band is identified. The bands of $CH_2$ of the side chains of the lysyl residues are visible from 2850 to 3000 $cm^{-1}$. The N—H bonds of the primary amines are between 3100 and 3300 $cm^{-1}$ (2 bands).

The zone of 700 to 1700 $cm^{-1}$ corresponds to the bands of deformation of the C=O carbonyls (1700 to 1600 $cm^{-1}$), called amide I. The C—N bond (1480 to 1520 $cm^{-1}$) is called amide II. The N—H bond, amide III, is in the zone between 1300 and 1400 $cm^{-1}$. These two major bands during the analysis of proteins (amide bonds) change based on the two-dimensional structure of the latter. At the end of the polylysine chain, there is a —COOH and an —NH$_2$.

Figure 2:
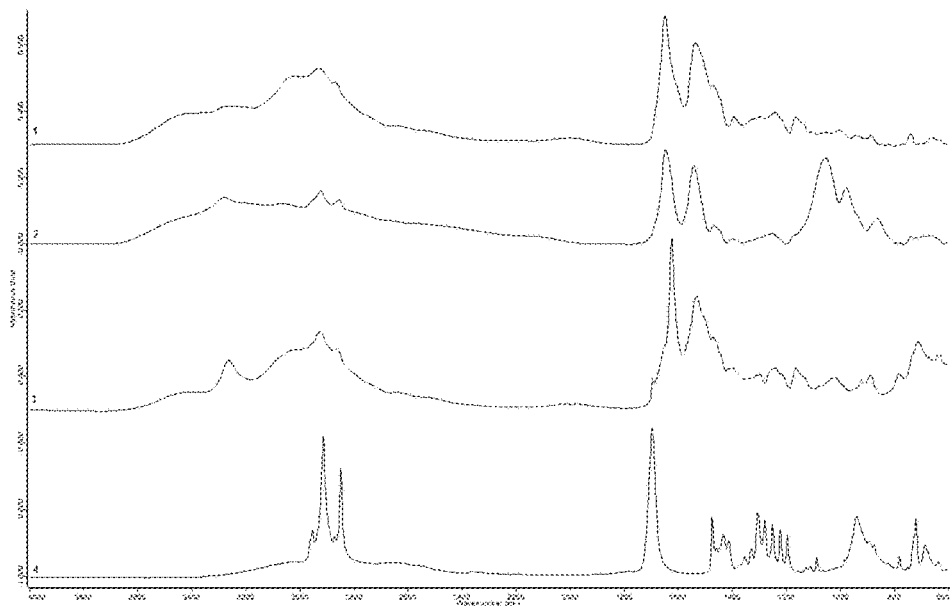
FIG. 2 shows multiple IR spectra: polylysine (1), the lauryl-polylysine compound (2), a polylysine+lauric acid mixture (3), and lauric acid (4).

FIG. 2 shows the spectrum of the PL (No. 1), of the lauryl-PLL compound (No. 2), of the PL+lauric acid mixture (No. 3), and of the lauric acid (No. 4).

The lauryl-PL compound (lauric acid grafted onto a PL) is shown by the following formula:

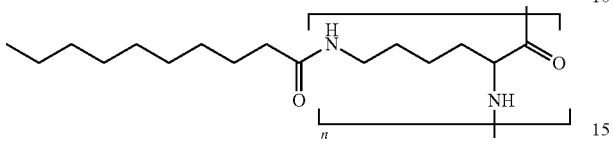

For the lauryl-PL compound, the results make it possible to affirm the presence of lauric acid and PL, using the comparison of different peaks. The peaks that are specific to the grafted lauric acid are at 1460 cm$^{-1}$ (C—CH$_3$) and at 2930 and 2860 cm$^{-1}$ (CH$_2$).

Figure 3:
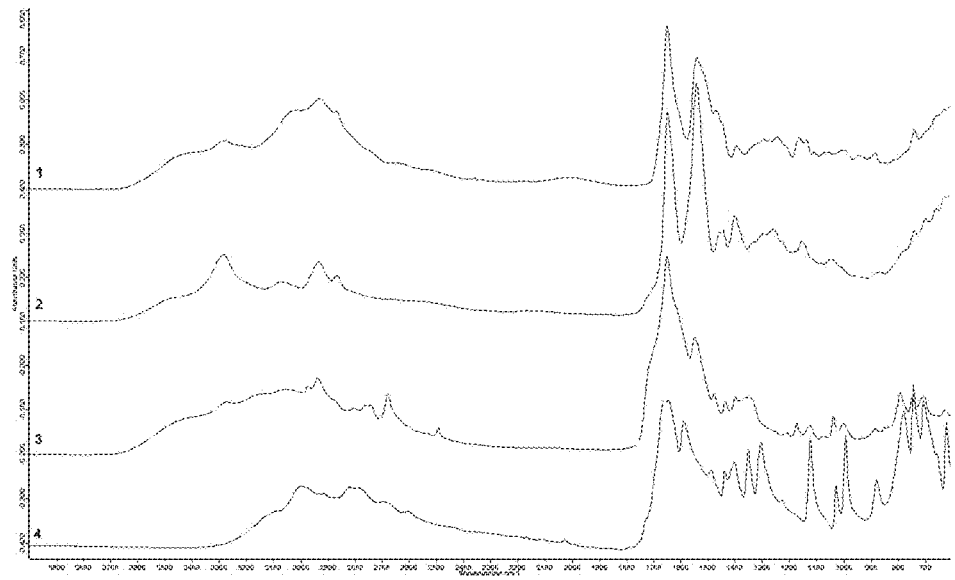
FIG. 3 shows multiple IR spectra: polylysine (1), the uric acid-glutaric anhydride-polylysine compound (2), a polylysine+uric acid mixture (3), and uric acid (4).

FIG. 3 shows the spectrum of the PL (No. 1), of the uric acid-GA-PL compound (No. 2), of the PL+uric acid mixture (No. 3), and of the uric acid (No. 4).

The uric acid-GA-PL compound is shown by the following formula:

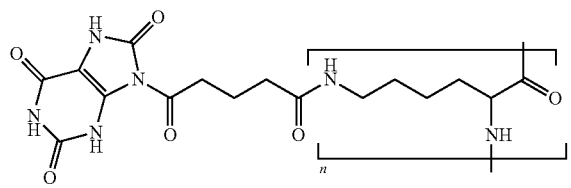

The peaks specific to the grafted uric acid are at 1255 cm$^{-1}$ (C—N cycle) and at 1455 cm$^{-1}$ (NH of the cycle). The increase in intensity of the peaks 2930 and 2865 cm$^{-1}$ corresponds to the CH$_2$ of the glutaric anhydride linker.

Figure 4:
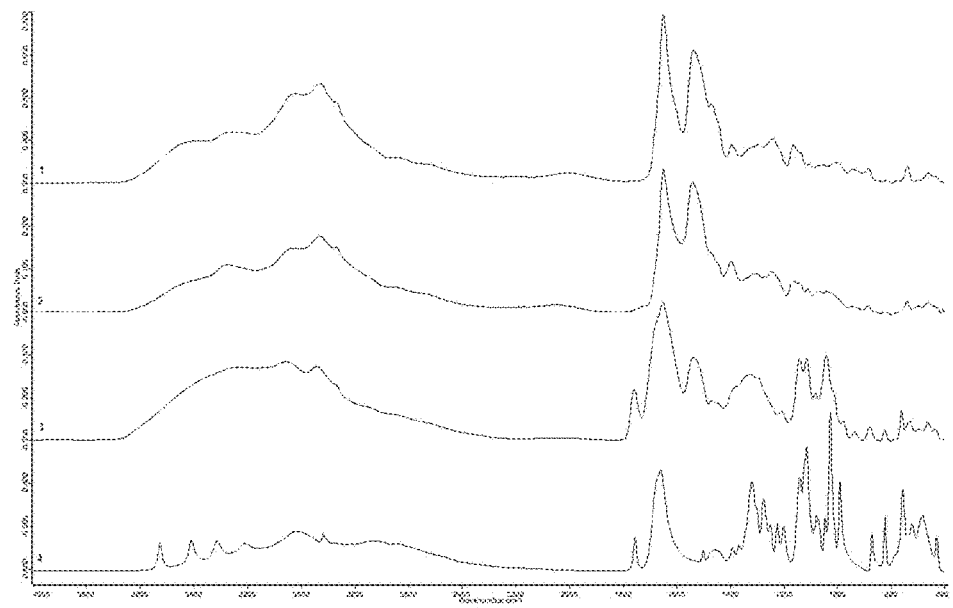
FIG. 4 shows multiple IR spectra: polylysine (1), the ascorbic acid-polylysine compound (2), a polylysine+ascorbic acid mixture (3), and ascorbic acid (4).

FIG. 4 shows the spectrum of the PL (No. 1), of the ascorbic acid-PL compound (No. 2), of the PL+ascorbic acid mixture (No. 3), and of the ascorbic acid (No. 4).

The ascorbic acid-PL compound is shown by the following formula:

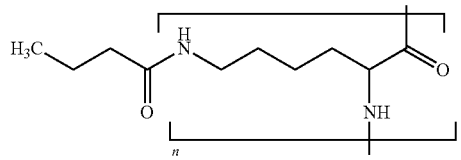

The PL+ascorbic acid mixture makes it possible to affirm, using differences in peaks, that the spectrum of the ascorbic acid-PL compound is the spectrum of the ascorbic acid grafted onto the PL.

The peaks specific to the grafted ascorbic acid are at 3290 cm$^{-1}$ (—OH), at 1370 cm$^{-1}$ (—OH), and at 1250 cm$^{-1}$ (C—O—C).

Figure 5:
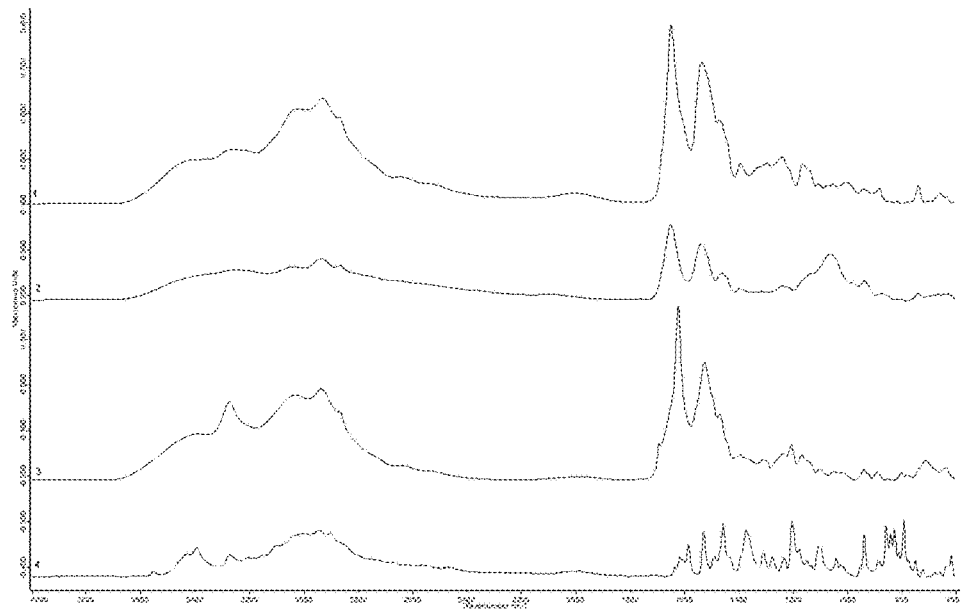
FIG. 5 shows multiple IR spectra: polylysine (1), the 5-hydroxytryptamine-G-polylysine compound (2), a polylysine+5-hydroxytryptamine mixture (3), and 5-hydroxytryptamine (4).

FIG. 5 shows the spectrum of the PL (No. 1), of the 5-hydroxytryptamine-G-PL compound (No. 2), of the PL+5HT mixture (No. 3), and of the 5HT (No. 4).

The 5HT-G-PL compound is shown by the following formula:

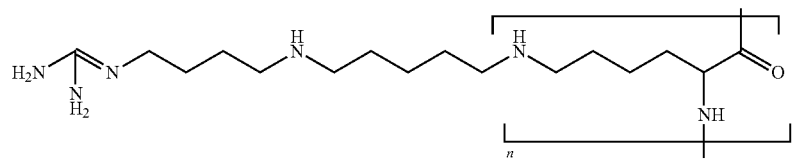

The peaks specific to the grafted 5HT are at 1335 cm$^{-1}$ (nitrogen-containing C—N cycle), at 1310 cm$^{-1}$ (linked —OH), and at 1020-1080 (C—O). The increase in intensity of the peaks 2930 and 2865 cm$^{-1}$ corresponds to the CH2 of the glutaraldehyde linker.

Identification of the Secondary Structure by Infrared

With the PL compounds being studied in vitro and in vivo, their anti-bacterial activity can be demonstrated according to the secondary structure.

The technique of circular dichroism by IR makes it possible to determine with precision the secondary structure of a substituted polylysine compound.

The Fourier Transform IR spectroscopy is a method that can also be used for the experimental determination of the secondary structure of a polylysine. The spectral zone studied going from 1400 to 1800 cm$^{-1}$ corresponds to the amides I and II of the PL or of the PL compound. The spectral treatment provided is to carry out the second derivative, thus studying the unordered or ordered formation of the PL compounds.

Figure 6:
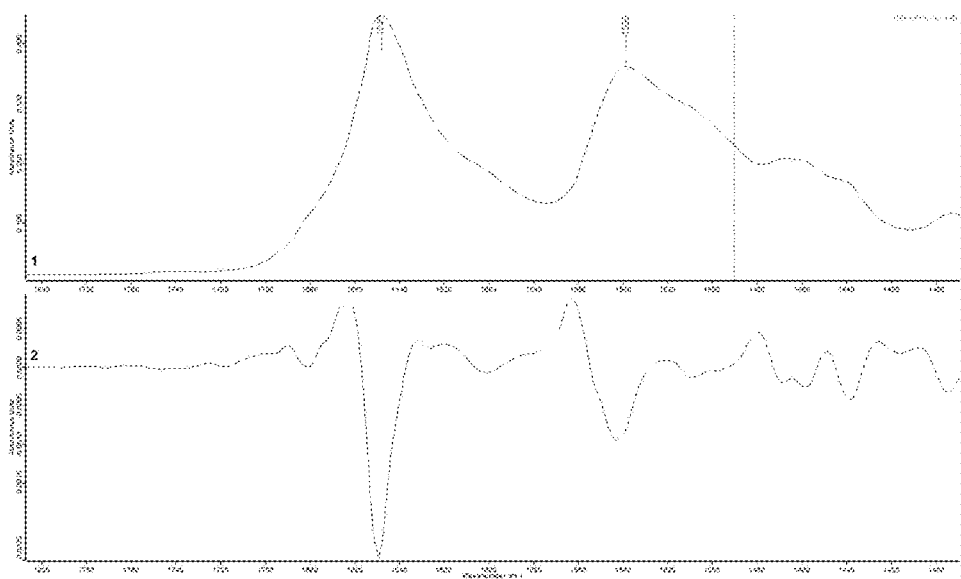
FIG. 6 shows the IR spectra of secondary structures of polylysine.

In FIG. 6, it is noted that the PL has an unordered secondary structure, spectral zoom of the amine zone of the PL (No. 1), zoom of the second derivative of the PL (No. 2).

Figure 7:
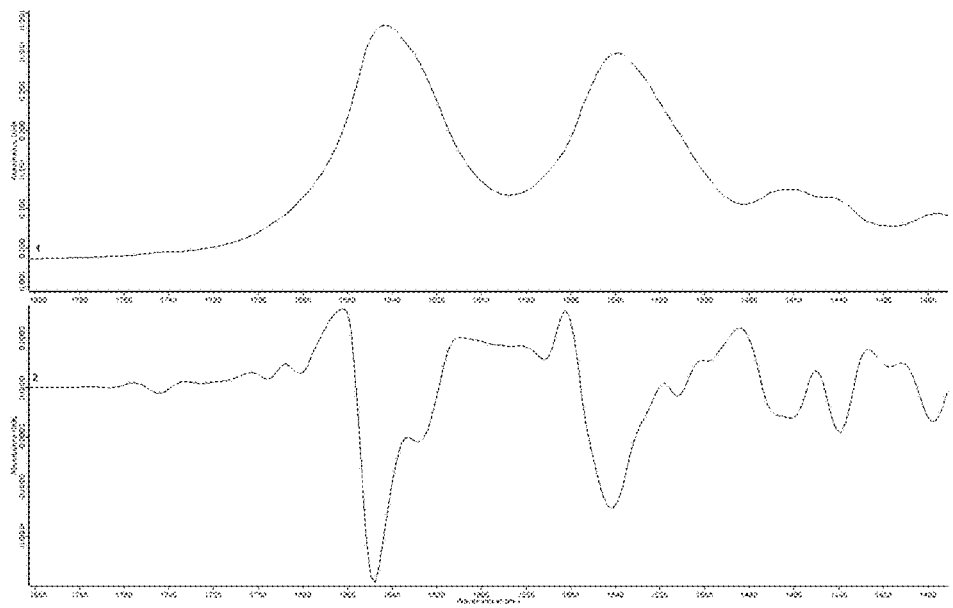
FIG. 7 shows the IR spectra of secondary structures of lauryl-polylysine.

In FIG. 7, the analyzed compound is lauryl-PL. The second derivative informs us of an ordered structure, spectral zoom of the amine zone of the lauryl-PL (No. 1), zoom of the second derivative of the lauryl-PL (No. 2).

Example for the Fatty Acid-PL Compounds

The quantification of each lysine monomer residue linked to a fatty acid (B) makes it possible to estimate the weight of the product by percentage. This method applies to the fatty acids starting from C2.

The calculation is as follows:

$$M_W^{PL-B} = M_W^{PL} + [M_W(PL-B) - M_W(PL)]x$$

with:

$M_W^{PL-B}$ total molecular weight of the fatty acids grafted onto the polylysine $M_W^{PL}$ total molecular weight of polylysine $M_w$(PL-B) molecular weight of lysine residues linked with at least one fatty acid molecule by covalent bond $M_w$(PL) molecular weight of a lysine residue $M_w$(B) molecular weight of a fatty acid $A_{CH}$(PL-B) an IR zone of the CH zone of the spectrum of the PL-fatty acid compound $A_{CH}$(PL) an IR zone of the CH zone of the spectrum of the polylysine $A_{CH}$(B) an IR zone of the CH zone of the spectrum of the fatty acid The following table describes the IR standards that make it possible to accept or to refuse a batch of poly-L-lysine compounds:

| IR Standards Range of Conformity |
|---|
| Low value assumed in terms of percentage 5% |
| High value assumed in terms of percentage 25% |

Quantification by Visible UV

1/Example of the Ascorbic-PL Compound:

A volume of ascorbic acid-PL compound is diluted in an organic solvent or in an aqueous medium and then analyzed in the UV range.

The maximum of the molar absorption coefficient of the ascorbic acid $\xi$ is at $\varepsilon=254$ nm.

That of the ascorbic acid-PLL compound is at $\varepsilon=254\text{-}256$ nm.

$$[C_{254}] = \frac{(OD254 - OD600) \times \text{dilution factor}}{\varepsilon 254}$$

$OD_{254} = 0.727\varepsilon;\ OD_{500} = 0;\ \varepsilon_{254} = 13\,705;\ \text{dilution factor} = 20$ $[C_{254}] = 0.0010\ \text{mol/L}$ Based on the UV absorbency of the small molecules, the concentration is calculated using the Beer-Lambert law.

$$[C\varepsilon] = \frac{(OD\lambda - OD\ \text{bottom width}) \times \text{dilution factor}}{\varepsilon\lambda}$$

The following table describes the UV standards that make it possible to accept or to refuse a batch of poly-L-lysine compounds:

| UV Standards Range of Conformity |
|---|
| Low value assumed in terms of concentration: $10^{-3}$ mol/L |
| High value assumed in terms of concentration: $5 \cdot 10^{-2}$ mol/L |

2/Example of the 5HT-G-PL Compound:

A volume of the 5HT-G-PL compound is diluted in an organic solvent or in an aqueous medium and then analyzed in the UV range.

The maximum of the molar absorption coefficient of the 5HT, $\xi$ is at $\varepsilon 1=280$ nm and at $\varepsilon 2=300$ nm.

That of the 5HT-G-PLL compound is at $\varepsilon 1=275\text{-}280$ nm and at $\varepsilon 2=295\text{-}300$ nm.

$$[C_{280}] = \frac{(OD280 - OD600) \times \text{dilution factor}}{\varepsilon 280}$$

$OD_{280} = 0.765;\ OD_{500} = 0;\ \varepsilon_{280} = 5290;\ \text{dilution factor} = 20$ $[C_{280}] = 0.00289\ \text{mol/L}$ $OD_{300} = 0.649;\ OD_{500} = 0;\ \varepsilon_{300} = 4198;\ \text{dilution factor} = 20$ and $[C_{300}] = 0.00309\ \text{mol/L}$ and $[C_{average}] = 0.00299\ \text{mol/L}$ According to the absorbency of the small molecules in terms of UV, the concentration is calculated using the Beer-Lambert law.

$$[C_\varepsilon] = \frac{(OD\lambda - OD\ \text{bottom width}) \times \text{dilution factor}}{\varepsilon\lambda}$$

Quantification of PL-Fatty Acid Compounds

After the synthesis of the lauryl-PL compound and its purification by tangential ultra-filtering (UFT), acid hydrolysis is initiated on a sample of the compound for the purpose of quantification by gas phase chromatography of the lauryl that is linked in a covalent way to the PL.

Example of the Lauryl-PL Compound.

20 mg of lauryl-PL is added to a volume of 2 ml of a solution with 1 mg/ml of decanoic acid (internal standard) dissolved in methanesulfonic acid at 99%. This solution is stirred with a magnet and heated at 120° C. for 3 hours. In a volume of 2 ml of purified water, the preceding solution is poured by fractions, and then heated at 65° C. for 15 minutes. The mixture is thus rinsed by 3 ml of ethyl acetate and then 4 ml of water. The organic phase is thus recovered and analyzed by a chromatographic separation technique.

A control solution has also been prepared with a concentration of 0.4 mg/ml of fatty acids in ethyl acetate.

The technique used is gas phase chromatography with a flame ionization detector (FID). It will be possible to use a mass spectrometer detector for more precision in the determination of the peaks of the chromatogram.

The content of fatty acids to be metered is determined using a semi-capillary column of molten silica (30 meters and 0.53 mm in diameter), a hydrogen vector gas (flow rate of 4 ml/min), a pressure of 2.7 bars, a split of 22, a temperature of the injector and the detector of 250° C., a temperature of the furnace of 200° C., and then a rise in temperature of 5° C./minute up to 250° C., with a run time of 15 minutes.

The solution under examination is injected (2 µl) according to the preceding conditions, as well as the control solution (20 mg of the internal standard and 20 mg of fatty acids to be metered, dissolved in 50 ml of ethyl acetate). In the chromatograms, the first peak is that of ethyl acetate, and the following peaks are those of fatty acids from the shortest to the longest aliphatic chain. The content is between 5 and 30% of metered fatty acids.

Figure 8:
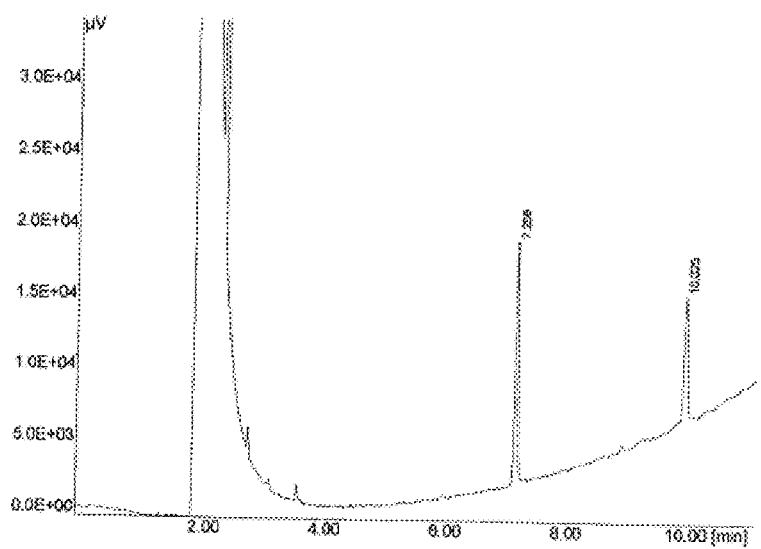
FIG. 8 shows the chromatogram of the lauryl-polylysine compound.

The chromatogram of the lauryl-PL compound that is obtained is presented in FIG. 8.

It is noted that the retention time of the decanoic acid is 7.258 minutes, and the retention time of the grafted lauric acid is 10.025 minutes.

The calculation of the content of fatty acids to be metered is as follows:

$$T(\% \text{ m/m}) = \frac{10\% \times P_{EI} \times \frac{ASE}{AEIE}}{P_E \times \frac{AST \times P_{REI}}{AEIT \times P_R}}$$

ASE: area of the peak of the fatty acid in the chromatogram that is obtained with the solution under examination.

AST: area of the peak of the fatty acid in the chromatogram that is obtained with the control solution.

AEIE: area of the peak of the internal standard (decanoic acid) in the chromatogram that is obtained with the solution under examination.

AEIT: area of the peak of the internal standard (decanoic acid) in the chromatogram that is obtained with the control solution.

$P_E$: sampling of the lauryl-PLL compound for the production of the solution under examination.

$P_{EI}$: sampling of the internal standard (decanoic acid) for the production of the solution under examination.

$P_{REI}$: sampling of the internal standard (decanoic acid) for the production of the control solution.

$P_R$: sampling of the fatty acid (lauric acid) to be metered for the production of the control solution.

According to the results of chromatograms on fatty acid-PL compounds, the content of grafted fatty acids is confirmed by a grafting percentage on the PL.

T (% m/m): grafting percentage

It is possible to determine a standard and a range of conformity.

| GPC Standards Range of Conformity |
| --- |
| Low value assumed in terms of percentage: 5% |
| High value assumed in terms of percentage: 20% |

The invention claimed is:

1. A method for identification and characterization of compounds that conjugate at least one polylysine and at least one other molecule that is selected from the group consisting of acids, fatty acids, vitamins, amino acids, metabolic derivatives of amino acids that have a neutrotransmitter activity, and active substances, comprising at least:
   one step for identification by infrared spectroscopy, and
   at least one step for characterization selected from the group consisting of:
   absorption spectroscopy in the visible ultraviolet,
   gas phase chromatography, and
   high-performance liquid phase chromatography.

2. The method according to claim 1, wherein said molecule is a molecule that has a molecular weight that is less than 900 g/mol.

3. The method according to claim 2, wherein the polylysine is a poly-L-lysine.

4. The method according to claim 2, further comprising a step for detecting residual solvents and/or at least one microbiological control by identification of microorganisms on an agar medium.

5. The method according to claim 2, wherein the infrared spectroscopy is a Fourier Transform Infrared spectroscopy.

6. The method according to claim 1, wherein the polylysine is a poly-L-lysine.

7. The method according to claim 6, further comprising a step for detecting residual solvents and/or at least one microbiological control by identification of microorganisms on an agar medium.

8. The method according to claim 6, wherein the infrared spectroscopy is a Fourier Transform Infrared spectroscopy.

9. The method according to claim 1, further comprising a step for detecting residual solvents and/or at least one microbiological control by identification of microorganisms on an agar medium.

10. The method according to claim 1, wherein the infrared spectroscopy is a Fourier Transform Infrared spectroscopy.

11. The method according to claim 1, wherein the step for identification by infrared spectroscopy is implemented with at least one characteristic selected from the group consisting of:
   spectral range of between 400 and 4000 cm$^{-1}$,
   a spectral intensity in terms of transmission or absorbency,
   a resolution of between 1 and 8 cm$^{-1}$, and
   a number of spectral scans carried out by the Fourier Transform Infrared spectrometer of between 10 and 20, for each analyzed sample.

12. The method according to claim 1, wherein the step for identification by infrared spectroscopy consists in comparing the spectrum that is obtained for the polylysine/molecule conjugate with the spectrum of the polylysine and the spectrum of the molecule by itself.

13. The method according to claim 1, wherein the compounds that are to be identified and characterized are compounds that conjugate at least one polylysine and at least one acid and/or at least one fatty acid, and further comprising at least one infrared spectroscopy step, and a gas phase chromatography step preceded by acid hydrolysis.

14. The method according to claim 1, wherein the compounds that are to be identified and characterized are compounds that conjugate at least one polylysine and at least one vitamin, and further comprising at least one infrared spectroscopy step, and:
   a step of absorption spectroscopy in the visible ultraviolet, and/or
   a step of gas phase chromatography or a step of high-performance liquid phase chromatography.

15. The method according to claim 1, wherein the gas phase chromatography step is carried out with at least one characteristic selected from the group consisting of:
   implementation on a semi-capillary column of molten or capillary silica,
   use of a hydrogen or helium vector gas with a flow rate of between 1 and 4 ml/minute,
   a pressure of between 2 and 3 bars,
   a split mode, a temperature of the injector and the detector of between 80 and 300° C., a temperature of the furnace of between 200 and 250° C.,
   a rise in temperature of between 10 and 20° C./minute,
   an injected volume of 2 to 20 µl, and
   a flame ionization detector or mass spectrometer.

16. The method according to claim 1, wherein the compounds that are to be identified and characterized are compounds that conjugate at least one polylysine and at least one amino acid, further comprising at least one infrared spectroscopy step and one high-performance liquid phase chromatography step.

17. The method according to claim 1, wherein the compounds that are to be identified and characterized are compounds that conjugate at least one polylysine and at least one metabolic derivative of amino acids that have a neurotransmitter activity, further comprising at least one infrared spectroscopy step, and:
- a step of absorption spectroscopy in the visible ultraviolet, and/or
- a step of high-performance liquid phase chromatography.

18. The method according to claim 1, wherein the high-performance liquid phase chromatography step is preceded by acid hydrolysis or derivatization.

19. The method according to claim 1, wherein the high-performance liquid phase chromatography step is carried out with at least one characteristic selected from the group consisting of:
- implementation on a column in normal or reverse phase with a diameter of between 4 and 20 mm, with a length of between 15 and 30 cm,
- use of a polar or slightly polar mobile phase,
- an isocratic mode or gradient,
- an injected volume of 10 to 100 μl, and
- a fluorescence detector or visible UV detector.

20. The method according to claim 1, wherein the UV/visible spectroscopy step is carried out with at least one characteristic selected from the group consisting of:
- implementation on a double-beam spectrometer,
- a spectral range of between 200 and 700 nm,
- a spectral intensity in terms of absorbency,
- a bandwidth of between 1 and 4 nm,
- an acquisition speed of between 120 and 480 nm/minute, and
- a volume used of between 700 μl and 2 ml.

* * * * *